US006316188B1

(12) United States Patent
Yan et al.

(10) Patent No.: US 6,316,188 B1
(45) Date of Patent: Nov. 13, 2001

(54) HISTAMINE-N-METHYLTRANSFERASE VARIANTS ASSOCIATED WITH HISTAMINERGIC DISEASE

(75) Inventors: Lan Yan, Rochester, MN (US); Stephen Liggett, Cincinnati, OH (US); Raymond E. Galinsky, Zionsville, IN (US); Richard M. Weinshilboum, Rochester, MN (US); Herb M. Lachman, New York, NY (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 09/162,274

(22) Filed: Sep. 29, 1998

(51) Int. Cl.[7] ............................... C12Q 1/68; C07H 21/04
(52) U.S. Cl. .............................. 435/6; 536/23.2; 536/23.5
(58) Field of Search ................................. 435/6; 536/23.2, 536/23.5

(56) References Cited

PUBLICATIONS

Preuss et al., "Human Histamine N–Methyltransferase Pharmacogenetics: Common Genetic Polymorphisms that Alter Activity", *Mol. Pharmacol.*, 1998, 53(4):708–717.

Scott et al., "Pharmacogenetics of N–methylation: Heritability of human erythrocyte histamine N–methyltransferase activity", *Clin. Pharmacol. Ther.*, 1988, 43(3):256–262.

Price et al., "Genetic Segregation Analysis of Red Blood Cell (RBC) Histamine N–Methyltransferase (HNMT) Activity", *Genet. Epidemiol.*, 1993, 10(2):123–131.

Rose et al., "An Open–Label Study of the Therapeutic Efficacy of High–Dose Famotidine Adjuvant Pharmacotherapy in Schizophrenia: Preliminary Evidence for Treatment Efficacy", *Clin. Neuropharmacol.*, 1996, 19(4):341–348.

Prell et al., "Histamine metabolites in cerebrospinal fluid of patients with chronic schizophrenia: their relationships to levels of other aminergic trasmitters and ratings of symptoms", *Schizophrenia Res.*, 1995, 14:93–104.

Lewis, "PCR's Competitors Are Alive and Well and Moving Rapidly Towards Commercializaton", *Genetic Engineering News*, 1992, 12(9):1.

Guatelli et al., "Isothermal, *in vitro* amplification of nucleic acids by a multienzyme reaction modeled after retoviral replication", *Proc. Natl., Acad. Sci. USA*, 1990, 87(5):1874–1878.

Weiss, R., "Hot Prospect for New Gene Amplifier", *Science*, 1991, 254(5036):1292–1293.

Preuss et al., "Human Histamine N–Methyltransferase (HNMT) Molecular Pharmacogenetics", *J. Inv. Med.*, 1997, 45(3):237A.

Yamauchi, K. et al., "Structure and function of human histamine N–methyltransferase: critical enzyme in histamine metabolism in airway", *Am J. Physiol.*, 1994, 267(3):L342–L349.

Van Loon et al., "Thiopurine Methyltransferase Isozymes in Human Renal Tissue", *Drugs Metab. Dispos.*, 1990, 18(5):632–638.

Van Loon et al., "Human Kidney Thiopurine Methyltransferase", *Biochem. Pharmacol.*, 1992, 44(4):775–785.

Kohler et al., "Continuous cultures of fused cells secreting antibody of predefined specificity", *Nature*, 1975, 256(5512):495–497.

(List continued on next page.)

*Primary Examiner*—Carla J. Myers
*Assistant Examiner*—Diana Johannsen
(74) *Attorney, Agent, or Firm*—Fish & Richardson P.C.

(57) ABSTRACT

Methods for characterizing patients diagnosed with histaminergic diseases are described. Nucleic acid molecules that include a histamine-N-methyltransferase intron variant sequence associated with a histaminergic disease also are described.

6 Claims, 4 Drawing Sheets

OTHER PUBLICATIONS

Kozbor et al., "The production of monoclonal antibodies from human lymphocytes", *Immunology Today*, 1983, 4(1):72–79.

Cote et al., "Generation of human monoclonal antibodies reactive with cellular antigens", *Proc. Natl. Acad. Sci USA*, 1983, 80(7):2026–2030.

Huse et al., "Generation of a Large Combinatorial Library of the Immunoglobulin Repertoire in Phage Lambda", *Science*, 1989, 246:1275–1281.

Hall et al., "Association of Glu 27 $\beta_2$–adrenoceptor polymorphism with lower airway reactivity in asthmatic subjects", *Lancet*, 1995, 345(8959):1213–1214.

Short Protocols in Molecular Biology, Chapter 8, Green Publishing Associates and John Wiley & Sons, Edited by Ausubel, F.M et al., 1992, 8–1—8–25.

Short Protocols in Molecular Biology, Chapter 11, Green Publishing Associates and John Wiley & Sons, Edited by Ausubel, F.M. et al., 1992, 11–1—11–54.

Cole et al., "The EBV–Hybridoma Technique and its Application to Human Lung Cancer", *Monoclonal Antibodies and Cancer Therapy*, Alan R. Liss, Inc., New York, 1985, 77–96.

Van Loon et al., "Human erythrocyte histamine N–methyltransferase: radiochemical microassay and biochemical properties", *Clin. Chem. Acta.*, 1985, 149(1):237–251.

Yan, L. et al, Immunogenetics 10:261–266, Apr. 2000.*

Yan, L. et al., Am. J. Med. Genet. 96(3):404–406, Jun. 2000.*

Sasaki, Y. et al. Immunogenetics 51:238–240, Mar. 2000.*

Girard, B. et al. Mol. Pharmacology 45(3):461–468, 1994.*

Aksoy, S. et al. Biochem. Biophys. 219:548–554. 1996.*

* cited by examiner

```
   1 atattgtcat ccatagctgc tctccaatgc acaaaactga gtactcatgg
  51 tatataggga ggcatatagg gacattcatc tctgttccta catctttgta
 101 aagactttgg cacagagaca atacttagta aatatgtttt aattgaactg
 151 aataattgtt tattatttct gccttatgat atcagaacta caataagctc
 201 tgaatataca tccaaaaaaa gagaatatat ttcagctaaa actgacttga
 251 cgaaatcaga gaacacagga agttctggat atttgcagat gaagtttaat
 301 aaataggaat aaaaggctca ataaaaaaga cacacgcaca cacacacaca
 351 cacacacaca cacacacaca cacacacaca caccaaatgg aagcagccag
 401 acaaaagcaa taagaacaa acaactaaaa ctatttgtgt attttaggg
 451 aaagaaaaag aaattgaaat cagaattaaa tgacaacatt tactggtcag
 501 cttatggaaa tatatgttgc ttgatggaaa tcaacctttc ctctgtgttt
 551 ctaaatatcc attacagaat taccctaact caagagactg tcatttagtg
 601 ataacttagt agaagttcct gataatggag atgaaagaaa tttgatttgg
 651 ggataaaaaa gaagagatat aagaacaaga gagttggatt tctttaaaaa
 701 atgtggagta tcccacacta aaacggtatc aaagaaaagt ttttttctgc
 751 aaatgtgata gccaagcatc aattgggagg gttgctgttt aaaaggcagc
 801 ctgtctggtt aagggagatg agccagaagg agatcactga agctttctgt
 851 ctgtcctctc cttacctgag taaggaagga ggaaaatcat tgtgtgttat
 901 ttttagtgca gtgagaaaaa gaaaatctgg cttacatcat gttgaaaaca
 951 aaagtaacac catatgttgt gcccaccgag agccattatg ataatgcatt
1001 agtcgggaag tgcataattg ctcagctcag aaatggcacc gagtcacagc
1051 actgacacca gcaaattttt tgcaattagt gtttggttct tttttctctg
1101 ccaggttaaa aataataata atgatgataa cagagcctct cttcaaccac
1151 tgaaatgctg attttcttgt aatgtcttgt ttgccggcaa actcttattt
1201 aggaagacaa tccactgtct ttggaataaa agatttttaa ataaatactc
1251 acaaccctca tttattttca ttgaacagag gttttattct ttctgcttca
1301 ttccaattcc accttctcct agagcatatc ctgcagttac ctctccctct
1351 tctgaaatat aagtagaaca tcaattatcn taggctattt attatttagc
1401 ctattatttg tcttggttca tctcttgagt taaattagat cttgggaact
1451 ttagcttaat ccatgcatga gcgccaaggg tctttgagca ttctataatc
1501 ttatgcagaa ctgtgtgggt atgtattgtt tgtgtatttt tctggagagt
1551 cagttactct cactagatca taaaggggac ttgggaacca aaagtatctc
1601 aagacattta atcctagaag cacaaagaaa gtataagttg tctcttatat
```

FIG. 3A

```
1651 tgcttttgcc aaatccagtt taacacttca gtaacgttaa ctattgtgtc
1701 atggttctaa gggtgtttac tttattaact cagtgaatcc ttgtagcagt
1751 ctataaatgg attatattat cacccctgtt ttacagatga taaaacttga
1801 gacacaggtt cataaagttg gtaagaagga aagccaggct tcatactcag
1851 ggcagttggg ttttagagac catgctcttt agtactgccc tgtactgact
1901 gtgtatgtaa tatgcatgta ttagaaggcc cataaataga aactcattat
1951 tattattata gatttctgaa tagcaggctt gcttttttag tctcaagaat
2001 gcaatcagtg gaaatacact agcaaactaa ttcatgtatt ttataagcac
2051 ttattacaca tctttcatgt gcgtaccatt acgcaataat tcacttaaat
2101 tatctcatgt aatgcttgta gttgcattca aggtaagttt gataatcccc
2151 attttacaga tgaggaaatt taagttctga gaggctagat aacaagcctc
2201 atctcattca tagagcatca gaagaagagt tcagctcatg tctgtctccc
2251 tcagataagg tattccgtag cttctctgca gggttagaat ttcagtttag
2301 tactacaaac attgctaaaa ggtcttctaa acttggggac aagatttata
2351 gaaacccaac ttagttattg tcaggtccaa ggcagcatct ttttttatat
2401 agagatgaga gtaaaaantc attgatttga gtaaatcacc atntactgtg
2451 ctctttgttt ccattattaa ttttcactgt taaagattct tgtctgaatt
2501 ccagactaac aactaccttc ctcatatcac cacctgaatg tccagtaggt
2551 atctcaaatt tatattcctg aaaccagagg cctgatgata caaaactgct
2601 ngtcttcatt cttctctcca acaatggcaa ttctgtcttc tcaggcgccc
2651 tcacagaaat tactggggtc atcactgatt ctttctttt acccatatcc
2701 tacatccaaa ttgttggcga gccctgttgg atctcggagt ataacacata
2751 aaaactccca ccacttctct tcacctccca gctcactggt ctgtgggacc
2801 caccccacc tatccccag gtgattacag tagccttctc gctgttctcc
2851 ccacctcntg cccttatgcg ccagtactct cttcccatcg gtgaggccag
2901 ggtgacctta ttaaatgtat attgagtcat tctaatgtgc tgttccatac
2951 agaaaccatg ttttagtagt gaagttgaaa ctgaaattaa tttaaatgaa
3001 tgaaacttaa aattcaggtc ttcagtaaca cttgaaactc aagtcctaag
3051 ccacctttca agtgctccat agcaacaagt ggtgagtgac aatcctgctg
3101 gacaatgcag atatcgaacg tgtccattgg ttcagaaaat tctatcagac
3151 agcattacag tggtttccca ttgggcccca agtgatctgg gccttcatc
3201 cactccccac ccctaatctc tccaacctca tctctttcc ctctgccctc
3251 actcattcag ccccaatttc actggcttcc tggctagttc tttaatgggc
```

FIG. 3B

```
3301 caagtatcat cctgtattca ggtcatgtgc agntgctcat ctctctcctg
3351 gagtcatctt cccctgata tcgccatgtc ttgctgtcag gtctctgctc
3401 aaatgtcagg ttattagaca gactntgcga ccaccctagt taaaacagca
3451 gcccatcaaa gtctttaacc ctcttagcat ttactcagat tacttttca
3501 tttagcattt atcaccatat atttacttat ttttctctct cctcctgtac
3551 tccttgaaat atgagctgca caaaggacaa gattattatt ntgttctatt
3601 ctaagcatct agtgtacttt ctngcagact gcaaatgaaa gaaagaataa
3651 atgaaagcat gacttctctt ttattgcaca ggaagcagtg gctgggacaa
3701 gctgtggaaa aagtacggat cacgctttcc ccaggatgac
```

EXON 6

FIG. 3C

```
                              SEQUENCE LISTING

<160> NUMBER OF SEQ ID NOS:  6

<210> SEQ ID NO 1
<211> LENGTH: 26
<212> TYPE: DNA
<213> ORGANISM: Artificial Sequence
<220> FEATURE:
<223> OTHER INFORMATION: PCR primer

<400> SEQUENCE: 1
attttgaaca actgaatcac tcaatt                                          26

<210> SEQ ID NO 2
<211> LENGTH: 32
<212> TYPE: DNA
<213> ORGANISM: Artificial Sequence
<220> FEATURE:
<223> OTHER INFORMATION: PCR primer

<400> SEQUENCE: 2
gaaaaacgtt ctttctatct gtttgtatat aa                                   32

<210> SEQ ID NO 3
<211> LENGTH: 30
<212> TYPE: DNA
<213> ORGANISM: Artificial Sequence
<220> FEATURE:
<223> OTHER INFORMATION: PCR primer

<400> SEQUENCE: 3
ttggaatgtt aagagaatct tagtataata                                      30

<210> SEQ ID NO 4
<211> LENGTH: 22
<212> TYPE: DNA
<213> ORGANISM: Artificial Sequence
<220> FEATURE:
<223> OTHER INFORMATION: PCR primer

<400> SEQUENCE: 4
ggctcaataa aaaagacaca cg                                              22

<210> SEQ ID NO 5
<211> LENGTH: 21
<212> TYPE: DNA
<213> ORGANISM: Artificial Sequence
<220> FEATURE:
<223> OTHER INFORMATION: PCR primer

<400> SEQUENCE: 5
tagggtaatt ctgtaatgga t                                               21

<210> SEQ ID NO 6
<211> LENGTH: 3740
<212> TYPE: DNA
<213> ORGANISM: Homo sapiens
<220> FEATURE:
<221> NAME/KEY: misc_feature
<222> LOCATION: (1)...(3740)
<223> OTHER INFORMATION: n = A,T,C or G

<400> SEQUENCE: 6
```

-continued

```
atattgtcat ccatagctgc tctccaatgc acaaaactga gtactcatgg tatataggga    60
ggcatatagg gacattcatc tctgttccta catctttgta aagactttgg cacagagaca   120
atacttagta aatatgtttt aattgaactg aataattgtt tattatttct gccttatgat   180
atcagaacta caataagctc tgaatataca tccaaaaaaa gagaatatat ttcagctaaa   240
actgacttga cgaaatcaga gaacacagga agttctggat atttgcagat gaagtttaat   300
aaataggaat aaaaggctca ataaaaaaga cacacgcaca cacacacaca cacacacaca   360
cacacacaca cacacacaca caccaaatgg aagcagccag acaaaagcaa taagaacaa    420
acaactaaaa ctatttgtgt attttaggg aaagaaaaag aaattgaaat cagaattaaa    480
tgacaacatt tactggtcag cttatggaaa tatatgttgc ttgatggaaa tcaacctttc   540
ctctgtgttt ctaaatatcc attacagaat taccctaact caagagactg tcatttagtg   600
ataacttagt agaagttcct gataatggag atgaaagaaa tttgatttgg ggataaaaaa   660
gaagagatat aagaacaaga gagttggatt tctttaaaaa atgtggagta tcccacacta   720
aaacggtatc aaagaaaagt tttttctgc aaatgtgata gccaagcatc aattgggagg    780
gttgctgttt aaaaggcagc ctgtctggtt aagggagatg agccagaagg agatcactga   840
agctttctgt ctgtcctctc cttacctgag taaggaagga ggaaaatcat tgtgtgttat   900
ttttagtgca gtgagaaaaa gaaaatctgg cttacatcat gttgaaaaca aagtaacac    960
catatgttgt gcccaccgag agccattatg ataatgcatt agtcgggaag tgcataattg  1020
ctcagctcag aaatggcacc gagtcacagc actgacacca gcaaattttt tgcaattagt  1080
gtttggttct tttttctctg ccaggttaaa ataataata atgatgataa cagagcctct   1140
cttcaaccac tgaaatgctg attttcttgt aatgtcttgt ttgccggcaa actcttattt  1200
aggaagacaa tccactgtct ttggaataaa agatttttaa ataaatactc acaaccctca  1260
tttattttca ttgaacagag gttttattct ttctgcttca ttccaattcc accttctcct  1320
agagcatatc ctgcagttac ctctccctct tctgaaatat aagtagaaca tcaattatcn  1380
taggctattt attatttagc ctattatttg tcttggttca tctcttgagt taaattagat  1440
cttgggaact ttagcttaat ccatgcatga gcgccaaggg tctttgagca ttctataatc  1500
ttatgcagaa ctgtgtgggt atgtattgtt tgtgtatttt tctggagagt cagttactct  1560
cactagatca taaaggggac ttgggaacca aaagtatctc aagacattta atcctagaag  1620
cacaaagaaa gtataagttg tctcttatat tgcttttgcc aaatccagtt taacacttca  1680
gtaacgttaa ctattgtgtc atggttctaa gggtgtttac tttattaact cagtgaatcc  1740
ttgtagcagt ctataaatgg attatattat caccccctgtt ttacagatga taaaacttga  1800
gacacaggtt cataaagttg gtaagaagga aagccaggct tcatactcag ggcagttggg  1860
ttttagagac catgctcttt agtactgccc tgtactgact gtgtatgtaa tatgcatgta  1920
ttagaaggcc cataaataga aactcattat tattattata gatttctgaa tagcaggctt  1980
gctttttag tctcaagaat gcaatcagtg gaaatacact agcaaactaa ttcatgtatt   2040
ttataagcac ttattacaca tctttcatgt gcgtaccatt acgcaataat tcacttaaat  2100
tatctcatgt aatgcttgta gttgcattca aggtaagttt gataatcccc attttacaga  2160
tgaggaaatt taagttctga gaggctagat aacaagcctc atctcattca tagagcatca  2220
gaagaagagt tcagctcatg tctgtctccc tcagataagg tattccgtag cttctctgca  2280
gggttagaat ttcagtttag tactacaaac attgctaaaa ggtcttctaa acttggggac  2340
```

-continued

```
aagatttata gaaacccaac ttagttattg tcaggtccaa ggcagcatct tttttatat    2400
agagatgaga gtaaaaantc attgatttga gtaaatcacc atntactgtg ctctttgttt    2460
ccattattaa ttttcactgt taaagattct tgtctgaatt ccagactaac aactaccttc    2520
ctcatatcac cacctgaatg tccagtaggt atctcaaatt tatattcctg aaaccagagg    2580
cctgatgata caaaactgct ngtcttcatt cttctctcca acaatggcaa ttctgtcttc    2640
tcaggcgccc tcacagaaat tactggggtc atcactgatt ctttctttt acccatatcc    2700
tacatccaaa ttgttggcga gccctgttgg atctcggagt ataacacata aaaactccca    2760
ccacttctct tcacctccca gctcactggt ctgtgggacc cacccccacc tatcccccag    2820
gtgattacag tagccttctc gctgttctcc ccacctcntg cccttatgcg ccagtactct    2880
cttcccatcg gtgaggccag ggtgacctta ttaaatgtat attgagtcat tctaatgtgc    2940
tgttccatac agaaaccatg ttttagtagt gaagttgaaa ctgaaattaa tttaaatgaa    3000
tgaaacttaa aattcaggtc ttcagtaaca cttgaaactc aagtcctaag ccacctttca    3060
agtgctccat agcaacaagt ggtgagtgac aatcctgctg gacaatgcag atatcgaacg    3120
tgtccattgg ttcagaaaat tctatcagac agcattacag tggtttccca ttgggcccca    3180
agtgatctgg gcccttcatc cactccccac ccctaatctc tccaacctca tctcttttcc    3240
ctctgccctc actcattcag ccccaatttc actggcttcc tggctagttc tttaatgggc    3300
caagtatcat cctgtattca ggtcatgtgc agntgctcat ctctctcctg gagtcatctt    3360
cccctgata tcgccatgtc ttgctgtcag gtctctgctc aaatgtcagg ttattagaca    3420
gactntgcga ccaccctagt taaaacagca gcccatcaaa gtctttaacc ctcttagcat    3480
ttactcagat tactttttca tttagcattt atcaccatat atttacttat ttttctctct    3540
cctcctgtac tccttgaaat atgagctgca caaaggacaa gattattatt ntgttctatt    3600
ctaagcatct agtgtacttt ctngcagact gcaaatgaaa gaaagaataa atgaaagcat    3660
gacttctctt ttattgcaca ggaagcagtg gctgggacaa gctgtggaaa aagtacggat    3720
cacgctttcc ccaggatgac                                                3740
```

HISTAMINE-N-METHYLTRANSFERASE VARIANTS ASSOCIATED WITH HISTAMINERGIC DISEASE

STATEMENT AS TO FEDERALLY SPONSORED RESEARCH

Funding for the work described herein was provided by the federal government, which has certain rights in the invention.

TECHNICAL FIELD

This invention relates to the association of histamine-N-methyltransferase gene variants with histaminergic diseases.

BACKGROUND OF THE INVENTION

Histamine plays a role in allergic responses, is involved in the regulation of gastric acid secretion and also is a neurotransmitter. Histamine is inactivated by oxidative deamination in a diamine oxidase catalyzed reaction or by N-methylation in a histamine N-methyltransferase (HNMT) catalyzed reaction. The product of the N-methylation, N-methylhistamine, is converted by monoamine oxidase to N-methyl imidazole acetic acid. HNMT is an S-adenosyl-L-methionine dependent cytosolic enzyme that contains 292 amino acids and has a relative molecular weight of 33 kDa.

N-methylation is the major process responsible for termination of the neurotransmitter actions of histamine in the brain as well as a major pathway for histamine metabolism in bronchial epithelium. HNMT also is expressed highly in the human kidney where a 6-fold interindividual variation in activity is observed. HNMT activity in human red blood cells varies as a result of a common genetic polymorphism. Scott, M. C. et al., *Clin. Pharmacol. Ther.*, 43:256–262 (1988); and Price, R. A. et al., *Genet. Epidemiol.*, 10:123–131 (1993). Approximately 70%–90% of the variance in activity is due to inheritance.

SUMMARY OF THE INVENTION

The invention is based on the discovery that polymorphisms within the HNMT gene are associated with histaminergic diseases. The methods described herein allow characterization of patients with histaminergic diseases, leading to a more accurate diagnosis and new avenues of therapy.

The invention features a method for characterizing a patient diagnosed with a histaminergic disease. The method includes determining if the patient has an HNMT gene variant associated with the histaminergic disease and characterizing the patient based on the determination. The histaminergic disease can be, for example, asthma, allergic asthma, allergy, schizophrenia and peptic ulcer disease. Characterizing the patient can include identifying a treatment regimen suitable for the patient based, at least in part, on the presence or absence of the variant in the patient. The HNMT gene variant can include, for example, a thymine at nucleotide 315 or a CA repeat polymorphism in intron 5.

The invention also features a method for determining a diagnosis or risk estimate of a histaminergic disease in a patient. The method includes detecting the presence or absence of an HNMT gene variant in the patient, and determining the diagnosis or risk estimate based, at least in part, on presence or absence of the variant in the patient.

The invention also features an isolated nucleic acid molecule including a HNMT intron sequence. The intron sequence includes a gene variant that is associated with a histaminergic disease and nucleotides flanking the gene variant. As used herein, "isolated nucleic acid" refers to a sequence corresponding to part or all of the HNMT gene, but free of sequences that normally flank one or both sides of the HNMT gene in a mammalian genome. The isolated nucleic acid molecule can be about 50 to about 120 nucleotides in length, about 54 to about 100 nucleotides in length, or about 70 to about 90 nucleotides in length. The gene variant can include a CA repeat, and in particular, can be located within intron 5 of the HNMT gene.

An oligonucleotide primer also is described. The oligonucleotide primer includes a nucleic acid molecule that causes elongation of a region of an HNMT intron having a gene variant. The gene variant is associated with a histaminergic disease. The primer can be about 14 to about 30 nucleotides in length. The nucleic acid primer can include the nucleotide sequence of SEQ ID NO:4 or SEQ ID NO:5. Kits containing oligonucleotide primers also are featured.

The invention also relates to an article of manufacture that includes packaging material and a nucleic acid molecule. The nucleic acid molecule specifically binds an HNMT gene variant, wherein the HNMT gene variant is associated with a histaminergic disease. The packaging material includes a label that indicates the nucleic acid molecule can be used for characterizing or diagnosing a histaminergic disease in the patient. The HNMT gene variant can include a thymine at nucleotide 315.

The invention also features a kit for characterizing or diagnosing a histaminergic disease in a patient. The kit includes an antibody that selectively binds an HNMT variant that is associated with the histaminergic disease.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The invention features a method for characterizing a patient diagnosed with a histaminergic disease. As used herein, "histaminergic disease" refers to a disease in which histamine plays a role in the pathophysiology of the disease. Non-limiting examples of histaminergic disease include allergy, asthma, including allergic asthma, peptic ulcer disease and neuropsychiatric disorders such as schizophrenia. The method includes determining if the patient has an HNMT gene variant associated with the histaminergic disease. As used herein, "gene variant" refers to any alteration in the wild-type gene sequence, and includes variations that occur in coding and non-coding regions of the gene.

Information obtained from this method can make it possible to subclassify patients with histaminergic disease. For example, determination of HNMT gene variants can help subclassify patients with bronchospasm and asthma based on risk factors responsible for the underlying pathophysiology. Thus, patients with histaminergic asthma could be treated with antihistamines, while patients with non-histaminergic asthma may not respond to such therapy. The presence or absence of HNMT gene variants also can be combined with other genetic risk factors to further classify patients to allow specific therapeutic regimens to be designed for an individual patient. In addition, the presence or absence of HNMT gene variants can be used to determine a risk estimate for the development of a histaminergic disease. Risk estimate indicates the relative risk a subject has for developing a histaminergic disease. For example, a risk estimate for development of asthma can be determined based on the presence or absence of HNMT gene variants. As described herein, a subject containing the exon 4 variant has a greater likelihood of having asthma. The odds ratio (calculated from statistical tests) of the exon 4 variant to asthma is approximately two. An odds ratio greater than one indicates a greater likelihood of disease. Additional risk factors include, for example, family history of atopy and other genetic factors such as polymorphisms within the interleukin-4 gene or the tumor necrosis factor alpha gene.

The HNMT gene variant can include, for example, a cytosine (C) to thymine (T) transition at nucleotide 315. This transition results in the substitution of isoleucine (Ile) for threonine (Thr) at amino acid 105 in exon 4. It has been observed that kidney samples with the allele encoding Ile105 have significantly lower HNMT activity and thermal stability than those with the Thr105 allele. Preuss, C. V. et al., *Mol. Pharmacol.*, 53(4):708–717 (1998). Thermal stability is typically measured as a heated/control (H/C) ratio and is a sensitive measure of differences in amino acid sequences. The studies presented below provide evidence for the first time that this nucleotide 315 variant is associated with histaminergic disease. In addition, the HNMT gene variant can include an adenosine (A) to guanosine (G) transition at nucleotide 939 in the 3' untranslated region. Frequencies of alleles encoding Thr and Ile105 were approximately 0.9 and 0.1, respectively, while frequencies for the nucleotide A939 and G alleles were approximately 0.8 and 0.2, respectively, in 127 human renal biopsy samples. These two polymorphisms are in linkage disequilibrium. Preuss, C. V. et al., 1998, supra.

As described herein, the exon 4 variant is associated with asthma, and in particular, allergic asthma, indicating that histamine metabolism is a factor involved in the pathophysiology of asthma. Asthma is a major public health problem that affects an estimated 150 million individuals worldwide, and multiple genes are thought to confer genetic susceptibility to asthma. Individual variation in HNMT activity may be an important factor in the diagnosis and treatment of asthma as HNMT plays the dominant role in histamine biotransformation in bronchial epithelium. Patients that have the exon 4 variant may have increased levels of histamine leading to bronchoconstriction, inflammation, and airway hyperresponsiveness. There have been conflicting reports with regard to the efficiency of antihistamines in the treatment of asthma. Assessment of JINMT genetic polymorphisms prior to therapy may improve the efficiency of treatment.

As described herein, another example of an HNMT gene variant includes a CA repeat polymorphism in intron 5. This polymorphism varies from about 12 to about 30 dinucleotide repeats. Subjects homozygous for the intron 5 allele having 20 CA repeats ($(CA)_{20}$) have higher HNMT activity than do subjects homozygous for the $(CA)_{21}$ allele. The intron 5 polymorphism is associated with schizophrenia and, in particular, chronic schizophrenia. Histamine in the central nervous system has been associated with wakefulness, suppression of seizures, hypothermia and emesis, and histaminergic projections innervate brain areas implicated in the pathophysiology of schizophrenia. H2 histamine-receptor antagonists such as famotidine significantly improve the efficacy of neuroleptic medication regimens. Rosse, R. B. et al., *Clin. Neuropharmacol.* 19:341–348 (1996). Levels of histamine metabolites, such as $N^\tau$-methylhistamine, are significantly increased in the cerebrospinal fluid of schizophrenic patients, suggesting increased central histaminergic activity in patients with chronic schizophrenia. Prell, G. D. et al., *Schizophrenia Res.*, 14:93–104 (1995).

HNMT gene variants can be assessed by sequencing exons and introns of the HNMT gene, by performing allele-specific hybridization, allele-specific restriction digests, mutation specific polymerase chain reactions (MSPCR), or by single-stranded conformational polymorphism (SSCP) detection. Polymerase chain reaction (PCR) refers to a procedure or technique in which target nucleic acids are amplified. Generally, sequence information from the ends of the region of interest or beyond is employed to design oligonucleotide primers that are identical or similar in sequence to opposite strands of the template to be amplified. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length. PCR is described, for example in *PCR Primer: A Laboratory Manual*, Ed. by Dieffenbach, C. and Dveksler, G., Cold Spring Harbor Laboratory Press, 1995. Nucleic acids also can be amplified by ligase chain reaction, strand displacement amplification, self-sustained sequence replication or nucleic acid sequence-based amplified. See, for example, Lewis, R. *Genetic Engineering News*, 12(9):1 (1992); Guatelli et al., *Proc. Natl. Acad. Sci. USA*, 87:1874–1878 (1990); and Weiss, R., *Science*, 254:1292 (1991). Genomic DNA is generally used in the analysis of HNMT gene variants.

Genomic DNA is typically extracted from peripheral blood samples, but can be extracted from such tissues as mucosal scrapings of the lining of the mouth or from renal tissue. Routine methods can be used to extract genomic DNA from a blood or tissue sample, including, for example, phenol extraction. Alternatively, genomic DNA can be extracted with kits such as the QIAamp® Tissue Kit (Qiagen, Chatsworth, Calif.), Wizard® Genomic DNA purification kit (Promega, Madison, Wis.) and the A.S.A.P.™ Genomic DNA isolation kit (Bochringer Mannheim, Indianapolis, Ind.).

For example, exons and introns of the HNMT gene can be amplified through PCR and then directly sequenced. This method can be varied, including using dye primer sequencing to increase the accuracy of detecting heterozygous samples. Alternatively, allele-specific hybridization can be performed. In this procedure, a nucleic acid molecule is selectively hybridized to the amplified nucleic acid product to detect a gene variant. Hybridization conditions are selected such that the nucleic acid molecule can specifically bind the sequence of interest, e.g., the variant nucleic acid sequence. Such hybridizations are performed under high stringency conditions as many of the gene variants include only a single nucleotide difference. High stringency conditions can include the use of low ionic strength solutions and high temperatures for washing. For example, nucleic acid molecules can be hybridized at 42° C. in 2×SSC (0.3M NaCl/0.03 M sodium citrate/0.1% sodium dodecyl sulfate (SDS) and washed in 0.1×SSC (0.015M NaCl/0.0015 M sodium citrate), 0.1% SDS at 65° C. Hybridization conditions can be adjusted to account for unique features of the nucleic acid molecule, including length and sequence composition.

Figure 1:
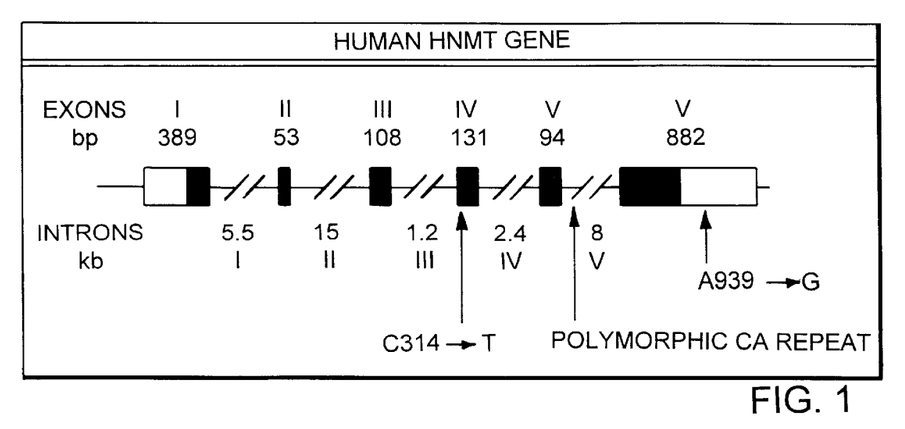
FIG. 1 is a representation of exon and intron lengths for the human HNMT gene. Filled rectangles represent exons and open rectangles represent untranslated sequence. Arrows indicate positions of nucleotide polymorphisms.

Allele-specific restriction digests can be performed in the following manner. The exon 4 region of the IJNMT gene, for example, can be amplified through PCR using a set of primers from either side of nucleotide 314. Primers that are from introns surrounding exon 4 (i.e., introns 3 and 4) are particularly useful (FIG. 1). The C314 allele is differentiated from the T314 allele by an EcoRV digestion of the exon 4 amplification product. For HNMT variants that do not alter a common restriction site, primers can be designed that introduce a restriction site when the mutant allele is present. For example, the A939G variant in the 3' UTR does not alter a restriction site. A MfeI site can be introduced when G939 is present using a mutagenic primer (e.g., 5'-ATT TTG AAC AAC TGA ATC ACT CAA TT-3', SEQ ID NO:1) to allow a MfeI digest to distinguish between the wild-type and mutant allele.

Certain variants, such as the intron 5 CA repeat polymorphism, change the size of the DNA fragment encompassing the polymorphism. As described above, alleles containing the intron 5 CA repeat polymorphism vary from about 12 to about 30 repeats. The number of repeats can be assessed by amplifying the region encompassing the polymorphism and determining the size of the amplified products by comparison with size standards. For example, the intron 5 CA repeat region can be amplified using a primer set from either side of the polymorphism. One of the primers is typically labeled, for example, with a fluorescent moiety, to facilitate sizing. The amplified products can be electrophoresed through acrylamide gels using a set of size standards that are labeled with a fluorescent moiety that differs from the PCR primer.

PCR conditions and primers can be developed that amplify a product only when the variant allele is present or only when the wild-type allele is present (MSPCR or allele-specific PCR). For example, patient DNA and a control can be amplified separately using either a wild-type primer or a primer specific for the variant allele. Each set of reactions is then examined for the presence of amplification products using standard methods to visualize the DNA. For example, the reactions can be electrophoresed through an agarose gel and DNA visualized by staining with ethidium bromide or other DNA intercalating dye. In DNA samples from heterozygous patients, reaction products would be detected in each reaction. Patient samples containing solely the wild-type allele would have amplification products only in the reaction using the wild-type primer. Patient samples containing solely the variant allele would have amplification products only in the reaction using the variant primer.

Mismatch cleavage methods also can be used to detect differing sequences by PCR amplification of a region of interest, followed by hybridization with the wildtype sequence and cleavage at points of mismatch. Chemical reagents, such as carbodiimide or hydroxylamine and osmium tetroxide can be used to modify mismatched nucleotides to facilitate cleavage.

Alternatively, HNMT variants can be detected by antibodies that have specific binding affinity for variant HNMT polypeptides. As used herein, "HNMT variant polypeptides" refer to HNMT polypeptides of any length, wherein the polypeptides include the variant amino acid sequence. HNMT variant polypeptides can be produced in various ways, for example, using recombinant techniques. The nucleic acid sequence of wild-type HNMT has a GenBank accession number of D16224 g532332. Yamauchi, K. et al., *Am. J. Physiol.*, 267:342–349 (1994). Amino acid changes can be introduced by standard techniques including oligonucleotide-directed mutagenesis and site-directed mutagenesis through PCR. See, *Short Protocols in Molecular Biology*, Chapter 8, Green Publishing Associates and John Wiley & Sons, Edited by Ausubel, F. M. et al., 1992.

A nucleic acid sequence encoding an HNMT variant polypeptide can be ligated into an expression vector and used to transform a bacterial or eukaryotic host cell. In bacterial systems, a strain of *Escherichia coli* such as BL-21 can be used. Suitable *E. coli* vectors include the pGEX series of vectors that produce fusion proteins with glutathione S-transferase (GST). Transformed *E. coli* are typically grown exponentially, then stimulated with isopropylthiogalactopyranoside (IPTG) prior to harvesting. In general, such fusion proteins are soluble and can be purified easily from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In eukaryotic host cells, a number of viral-based expression systems can be utilized to express HNMT variant polypeptides. A nucleic acid encoding an HNMT variant polypeptide can be cloned into, for example, a baculoviral vector and then used to transfect insect cells. Alternatively, the nucleic acid encoding an HNMT variant can be introduced into a SV40, retroviral or vaccinia based viral vector and used to infect host cells.

Mammalian cell lines that stably express HNMT variant polypeptides can be produced by using expression vectors with the appropriate control elements and a selectable marker. For example, the eukaryotic expression vector pCR 3.1 (Invitrogen, San Diego, Calif.) can be used to express HNMT polypeptides, for example, in COS cells. Following introduction of the expression vector by electroporation, DEAE dextran, or other suitable method, stable cell lines are selected. Alternatively, amplified sequences can be ligated into a mammalian expression vector such as pcDNA3 (Invitrogen, San Diego, Calif.) and then transcribed and translated in vitro using wheat germ extract or rabbit reticulocyte lysate. HNMT variant polypeptides can be purified by known chromatographic methods including DEAE ion exchange, gel filtration and hydroxylapatite chromatography. Van Loon, J. A. and R. M. Weinshilboum, *Drug Metab. Dispos.*, 18:632–638 (1990); Van Loon, J. A. et al., *Biochem. Pharmacol.*, 44:775–785 (1992).

Various host animals can be immunized by injection of an HNMT variant polypeptide. Host animals include rabbits, chickens, mice, guinea pigs and rats. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin and dinitrophenol. Polyclonal antibodies are heterogenous populations of antibody molecules that are contained in the sera of the immunized animals. Monoclonal antibodies, which are homogeneous populations of antibodies to a particular antigen, can be prepared using an HNMT variant polypeptide and standard hybridoma technology. In particular, monoclonal antibodies can be obtained by any technique that provides for the production of antibody molecules by continuous cell lines in culture such as described by Kohler, G. et al., *Nature*, 256:495 (1975), the human B-cell hybridoma technique (Kosbor et al., *Immunology Today*, 4:72 (1983); Cole et al., *Proc. Natl. Acad. Sci USA*, 80:2026 (1983)), and the EBV-hybridoma technique (Cole et al., "Monoclonal Antibodies and Cancer Therapy", Alan R. Liss, Inc., pp. 77–96 (1983). Such antibodies can be of any immunoglobulin class including IgG, IgM, IgE, IgA, IgD and any subclass thereof The hybridoma producing the monoclonal antibodies can be cultivated in vitro and in vivo.

Antibody fragments that have specific binding affinity for an HNMT variant polypeptide can be generated by known techniques. For example, such fragments include but are not limited to F(ab')$_2$ fragments that can be produced by pepsin digestion of the antibody molecule, and Fab fragments that can be generated by reducing the distilfide bridges of F(ab')$_2$ fragments. Alternatively, Fab expression libraries can be constructed. See, for example, Huse et al., *Science*, 246:1275 (1989).

Once produced, antibodies or fragments thereof are tested for recognition of HNMT variant polypeptides by standard immunoassay methods including ELISA techniques, radioimmunoassays and Western blotting. See, *Short Protocols in Molecular Biology*, Chapter 11, Green Publishing Associates and John Wiley & Sons, Edited by Ausubel, F. M et al., 1992. Antibodies can be conjugated to solid supports suitable for diagnostic assays, including, for example, beads, plates, slides or well formed from materials such as latex or polystyrene. Antibodies also can be conjugated to detectable groups such as radiolabels, enzyme labels and fluorescent labels.

The invention also features an isolated nucleic acid molecule including an HNMT intron sequence. The intron sequence includes a gene variant associated with a histaminergic disease and nucleotides flanking the gene variant. For example, the HNMT intron sequence can be from intron 5. In particular, the gene variant can include an intron 5 CA repeat polymorphism that is associated with a histaminergic disease. The nucleic acid molecule can be about 50 to 120 nucleotides in length, and in some embodiments can be from about 54 to about 100 nucleotides or about 70 to about 90 nucleotides in length. The nucleic acid molecules can be in the form of RNA or in the form of DNA. The DNA can be double-stranded or single-stranded.

As a result of the present invention, it is now possible to design oligonucleotide primers that can be used to detect HNMT gene variants. Such oligonucleotide primers include a nucleic acid molecule that causes elongation of a region of an HNMT intron having a gene variant. As used herein, "causes elongation" indicates that the oligonucleotide primers are capable of initiating nucleic acid synthesis through a sequence containing an intron gene variant under appropriate conditions. Such primers can be used to amplify intron nucleotide sequences. Amplification techniques include, as described above, PCR and ligase chain reaction. An oligonucleotide primer of the invention need not reflect the exact sequence of the HNMT intron, but must be sufficiently complementary to hybridize with the HNMT intron. For example, an oligonucleotide primer can incorporate a nucleotide sequence that encodes a restriction enzyme recognition site and still be used to amplify the intron sequence.

An oligonucleotide primer of the invention can be natural, cloned or synthetic and can be labeled by photochemical, biochemical, immunochemical, or chemical means. For example, useful labels include $^{32}$P, fluorescent dyes, electrondense reagents, reporter molecules and biotin. Labels can be used to capture the primer such that immobilization of either the primer or amplified product onto a solid support is simplified. Oligonucleotide primers can be sinle stranded or double stranded. If double-stranded, the oligonucleotide primer is generally treated to separate its strands prior to use.

The invention will be further described in the following examples, which do not limit the scope of the invention described in the claims.

EXAMPLES

Example 1

Association Between Exon 4 Polymorphism of the Human HNMT Gene and Asthma

A C314T variant for the human HNMT gene results in a Thr105Ile change in the amino acid sequence which significantly lowers HNMT activity. Allele-specific restriction digestion was used to determine allele frequencies for this polymorphism in DNA samples from 237 randomly selected, normal Caucasian blood donors (controls) and 63 Caucasian asthmatic patients. All studies were conducted under guidelines approved by the Institutional Review Boards at the participating institutions. The diagnosis of asthma was determined essentially as described by Hall et al., *Lancet*, 345:1213–1214 (1995), and was based on a standard respiratory symptom questionnaire, skin prick tests for five common aeroallergens, measurements of methacholine responsiveness, reversibility of bronchial obstruction and response to therapy. Nonallergic asthmatics failed to display positive skin tests. No patient in the asthma cohort had a history of cigarette smoking.

Genomic DNA was isolated from peripheral blood samples with the QIAamp blood kit (Qiagen Inc., Chatsworth, Calif.). To determine the C·:T transition at nucleotide 314 of exon 4 of HNMT gene, forward and reverse intron-based primers were constructed as follows: I3F(–119): GAAAAACGTTCTTTCTATCTGTTTG-TATATAA (SEQ ID NO:2); and I4R(191):TTGGAATGTTAAAGAGAATCTTAGTATAATA (SEQ ID NO:3). Nucleotide numbers were assigned on the basis of their locations within the HNMT cDNA, with the "A" in the ATG translation initiation codon designated +1. Positive numbers were assigned to nucleotides located 3' to that initial position. Intron primers were designated based on the initial 5' nucleotide within the intron. The C314 allele could be differentiated from the T314 allele by EcoRV digestion of the 310 bp exon 4 amplification product. The T314 variant was cleaved by EcoRV, while the C314 allele (wild-type) was not. Whenever allele-specific restriction digestion assays were performed, control samples of known genotype were included with each assay to assure that cleavage had occurred. Selected results were also confirmed by direct dye-primer chemistry DNA sequencing.

Distributions of allele and genotype frequencies for the HNMT C314T polymorphism in the control subjects, patients with asthma and the subset of patients with allergic asthma are listed in Table 1. The table lists the total number of subjects or alleles of each type, followed by frequencies in parentheses. Statistical analysis of the data was performed with Fisher's exact test and $\chi^2$ test. Genotype frequencies for all groups conformed to the predictions of the Hardy-Weinberg theorem. The T314 variant allele that encodes Ile105 and results in decreased HNMT activity was more common in patients with asthma (allele frequency=0.19) than in control subjects (allele frequency=0.08, $x^2$=12.40, p=0.001, odds ratio=2.62). These differences were accentuated when only patients with allergic asthma were included in the analysis (allele frequency=0.21, $x^2$=15.13, p=0.001, odds ratio=2.95). Similar results were obtained when genotype frequencies were compared. When the sum of the frequencies for the 314C/T plus the 314T/T genotypes were compared among these subjects, $x^2$ values were 12.88 and 15.71 for patients with asthma and allergic asthma, (p=0.001 in both cases) when compared with controls, with odds ratio values of 3.01 and 3.49, respectively. The T314 allele was not more prevalent in severe asthmatics (46%) when compared with those with mild or moderate asthma (42%). Similarly, indices of pulmonary function did not differ between subjects with and without the allele ($FEV_1$ predicted 64.5±3.0 vs. 63.4±2.6%; change in $FEV_1$ after bronchodilator 24.4±3.3 vs. 28.9±2.8%, mean ± SEM, respectively).

TABLE 1

Human HNMT Genotype and Allele Frequencies C314T Genetic Polymorphism

| Sample | N | Genotype Frequency | | | Allele Frequency | |
|---|---|---|---|---|---|---|
| | | C/C | C/T | T/T | C | T |
| Controls | 237 | 199 (0.84) | 37 (0.16) | 1 (0.00) | 435 (0.92) | 39 (0.08) |
| Asthma | 63 | 40 (0.63) | 22 (0.35) | 1 (0.02) | 102 (0.81) | 24 (0.19) |
| Allergic Asthma | 55 | 33 (0.60) | 21 (0.38) | 1 (0.02) | 87 (0.79) | 23 (0.21) |

EXAMPLE 2

Polymorphic Intron 5 CA Repeats

Figure 2:
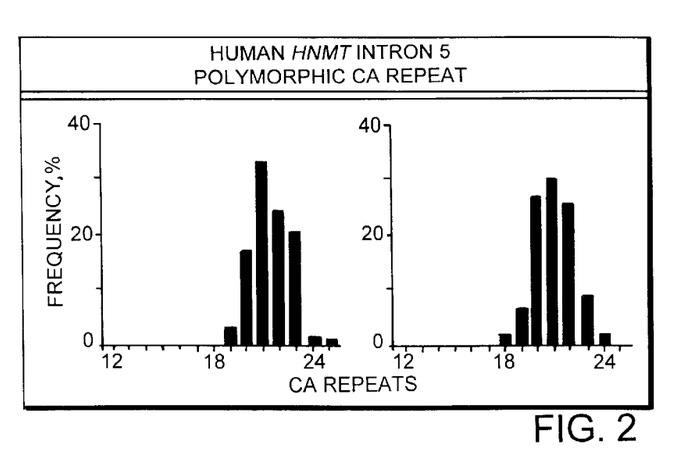
FIG. 2 is a frequency distribution of HNMT intron 5 polymorphic CA repeat alleles for (A) 113 human renal biopsy samples and (B) 249 blood donor samples.

Polymorphic intron 5 CA repeats were assayed by automated fluorescent scanning detection of DNA fragments (GeneScan). Specifically, a DNA fragment that included the region with the polymorphic CA repeat was amplified by PCR using a fluorescent (6-FAM)-labeled primer paired with an unlabeled primer. The nucleotide sequence of the 6-FAM primer is 5' GGC TCA ATA AAA AAG ACA CAC G-3' (SEQ ID NO:4). The nucleotide sequence of the unlabeled primer is 5'-TAG GGT AAT TCT GTA ATG GAT-3' (SEQ ID NO:5). Each amplification product was then electrophoresed with an aliquot of "size standards" that were labeled with a different fluorescent dye. Products were separated by electrophoresis through acrylamide slab gels with the ABI 377 DNA sequencer. The frequency distribution of CA repeat alleles in DNA from 113 human kidney biopsies and 249 blood donor samples is shown in FIG. 2. Alleles ranged in length from 12 to 25 repeats for the kidney samples (FIG. 2A), and from 13 to 25 repeats in length for the blood donor samples (FIG. 2B). Allele frequencies for the CA repeat length polymorphism in the renal samples were [repeat length (allele frequency)]: 12 (0.004); 19 (0.026); 20 (0.168); 21 (0.331); 22 (0.24); 23 (0.208); 24 (0.013); 25 (0.008). Allele frequencies for CA repeat length in the blood donor samples were similar to those in the renal samples. In both cases, $(CA)_{21}$ was the most common allele.

CA repeat length was correlated with HNMT phenotype as measured by the level of enzyme activity. HNMT activity was measured in red blood cell lysates as the conversion of histamine to radioactively labeled $N^\tau$-methylhistamine using [methyl-$^{14}$C]Ado-Met or [methyl-$^3$H]Ado-Met as the methyl donor. Van Loon et al., *Clin. Chem. Acta.*, 149:237–251 (1985). Final concentrations of histamine and Ado-Met in the reactions were 37.5 and 12.5 $\mu$M, respectively. In order to remove the effect of the exon 4 variant on phenotype, data from samples that were "wild-type" at exon 4 were used to study the CA repeat genotype-phenotype correlation. Values for HNMT activity were reported as mean ± SEM (Table 2). Samples from subjects homozygous for the $(CA)_{20}$ allele had higher average HNMT activity (39.3±3.79, nmole/hr/mg protein, p<0.01, n=5) than those from subjects homozygous for the $(CA)_{21}$ allele (29.7±1.67, n=24).

TABLE 2

Human HNMT Genotype Relationship of Intron 5 CA Repeat Polymorphism to Renal Phenotype

| CA Repeats | N (Homozygotes) | HNMT Activity (nmole/hr/mg protein) |
|---|---|---|
| 20 | 5 | 39.3 ± 3.8* |
| 21 | 24 | 29.7 ± 1.7* |
| 22 | 11 | 37.9 ± 2.9 |
| 23 | 16 | 30.8 ± 1.4 |

*p < 0.05 when compared with each other by ANOVA.

EXAMPLE 3

Figure 3C:
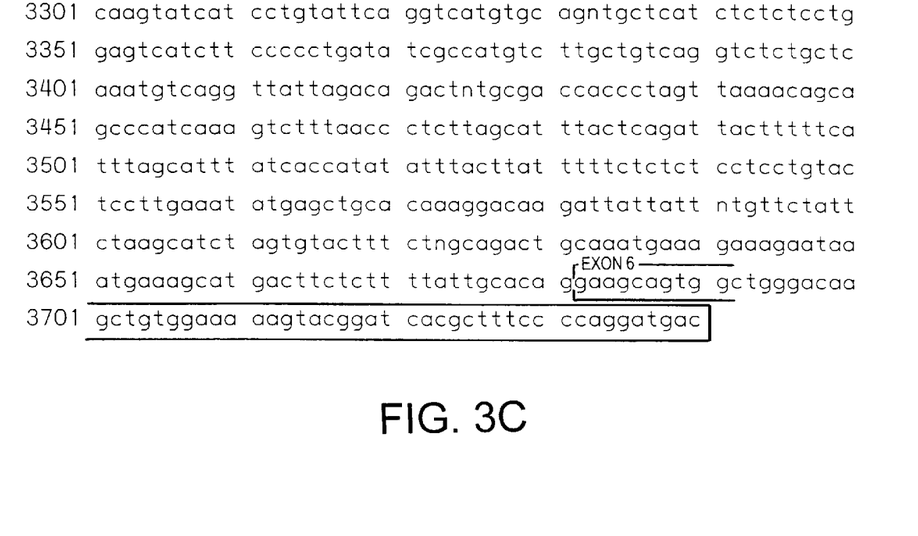
FIG. 3 is the partial nucleotide sequence of intron 5SEQ ID NO:6. PCR primers used to amplify the polymorphic CA repeat are indicated.

Association Between Polymorphic Intron 5 CA Repeats within the Human HNMT Gene and Schizophrenia The HNMT CA repeat in intron 5 was studied in DNA samples from human kidney biopsies (n=127), schizophrenic patients (n=92) and control subjects (n=52). Intron 5 CA repeat length was determined by PCR using a fluorescent labeled primer* paired with a nonlabeled primer, *15F(–3375): GGCTCAATAAAAAAGACACACG (SEQ ID NO:4), 15R(–3112): TAGGGTAATTCTGTAATGGAT (SEQ ID NO:5). FIG. 3 indicates the position of these primer sequences within the partial nucleotide sequence of intron 5 (approximately 3.1 kB). An approximately 360 bp PCR amplification product was then analyzed by use of the GeneScan Software package. Individuals homozygous for 21 CA repeats had significantly lower levels of HNMT activity (29.7+1.67 nmole/hr/mg protein, n=24) when compared with those homozygous for 20 CA repeats, (39.3±3.79 nmole/hr/mg protein, mean ± SE, n=5, p<0.01). The percentage of control subjects who were homozygous for 20 CA repeats was 9.6%, while the value for schizophrenics was 44.8%. All Chi-square analyses provided 2-tailed p-values of <0.0001. The data were most striking for those patients who were chronic in-patients when compared to outpatient schizophrenics.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of classifying a patient diagnosed with asthma, said method comprising determining if said patient has a histamine-N-methyltransferase gene variant associated with asthma, wherein said histamine-N-methyltransferase gene variant comprises a thymine at nucleotide 314; and classifying said patient as either having or lacking said histamine-N-methyltransferase gene variant associated with asthma.

2. The method of claim 1, wherein said histaminergic disease is allergic asthma.

3. A method of designing a treatment regimen from a patient diagnosed with asthma, said method comprising classifying said patient by the method of claim 1, designing a treatment regimen for said patient based, at least in part, on presence or absence of said histamine-N-methyltransferase variant.

4. A method for determining a diagnostic or risk estimate of asthma in a patient comprising detecting the presence or absence of a histamine-N-methyltransferase gene variant in said patient, wherein said histamine-N-methyltransferase gene variant comprises a thymine at nucleotide 314, and diagnosing or estimating risk of asthma based, at least in part, on presence or absence of said variant in said patient, wherein the presence of said histamine-n-methyltransferase gene variant is diagnostic of or indicative of risk for asthma.

5. The method of claim 1, wherein said histamine-N-methyltransferase gene variant results in a substitution of an isoleucine at amino 105.

6. The method of claim 4, wherein said histamine-N-methyltransferase gene variant results in a substitution of an isoleucine at amino acid 105.

* * * * *

UNITED STATES PATENT AND TRADEMARK OFFICE
CERTIFICATE OF CORRECTION

PATENT NO.    : 6,316,188 B1
DATED         : November 13, 2001
INVENTOR(S)   : Lan Yan et al.

It is certified that error appears in the above-identified patent and that said Letters Patent is hereby corrected as shown below:

<u>Title page,</u>
Item [56], "Prell" reference, please delete "trasmitters" and insert -- transmitters -- therefor.

<u>Column 15,</u>
Line 55, please delete "from" and insert -- for -- therefor.
Line 57, after "claim 1" please insert -- and --.

Signed and Sealed this

Fourth Day of February, 2003

JAMES E. ROGAN
*Director of the United States Patent and Trademark Office*